Figure 1:
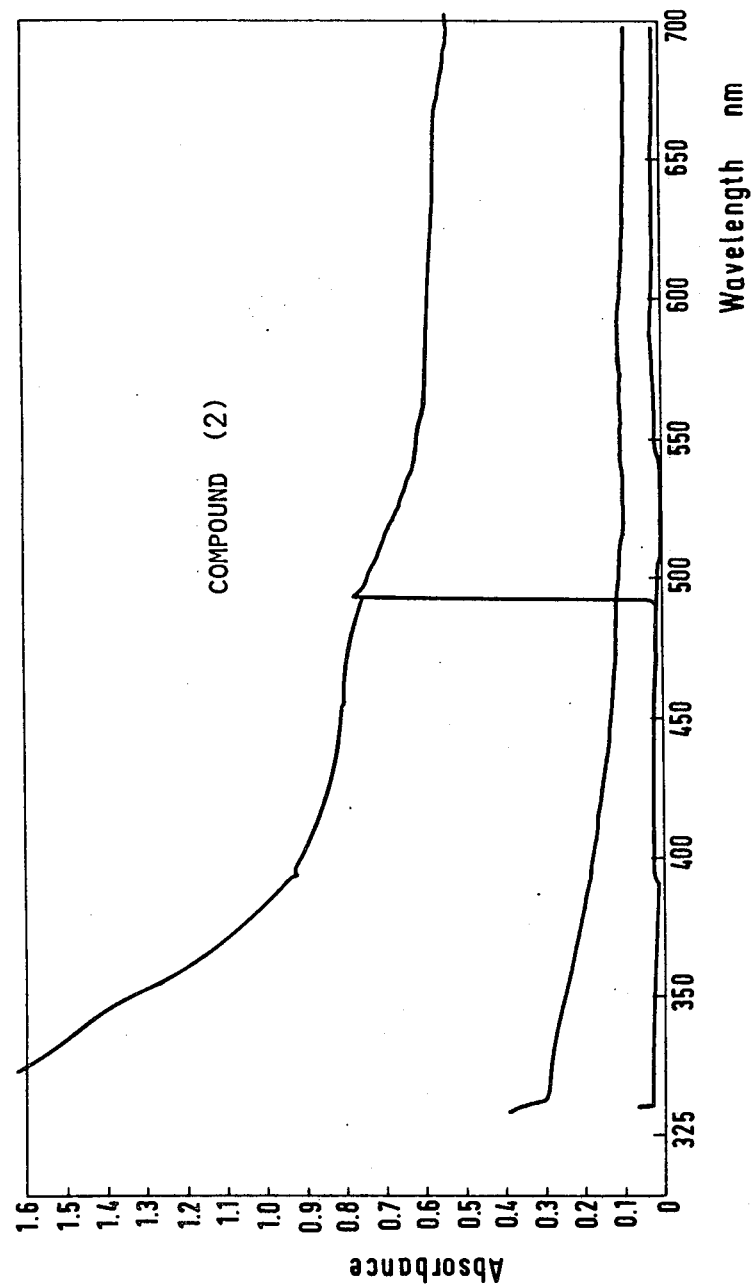

United States Patent [19]

Postle

[11] 4,439,518
[45] Mar. 27, 1984

[54] PROCESS FOR THE PRODUCTION OF A PHOTOGRAPHIC IMAGE

[75] Inventor: Stephen R. Postle, Brentwood, England

[73] Assignee: Ciba-Geigy A.G., Basel, Switzerland

[21] Appl. No.: 389,729

[22] Filed: Jun. 18, 1982

[30] Foreign Application Priority Data

Jun. 19, 1981 [GB] United Kingdom ............... 8119060

[51] Int. Cl.$^3$ .......................... G03C 5/24; G03C 1/02
[52] U.S. Cl. ..................................... 430/402; 430/565
[58] Field of Search ............... 430/402, 552, 549, 553, 430/384, 385, 565, 356

[56] References Cited

U.S. PATENT DOCUMENTS

| | | | |
|---|---|---|---|
| 3,271,178 | 9/1966 | Nadeau | 430/539 |
| 3,770,431 | 11/1973 | Gates | 430/214 |
| 4,126,461 | 11/1978 | Pupo | 430/402 |
| 4,252,893 | 2/1981 | Iwamuro et al. | 430/504 |

FOREIGN PATENT DOCUMENTS 1397868  6/1975  United Kingdom .

OTHER PUBLICATIONS

Henn et al, "Properties of Developing Agents IV. A Coupling Reaction of Cathecols," PSA Journal, Section B, vol. 19, pp. 146–148 (1953).
Ciurca et al, "Competing Couplers", Research Disclosure, Sep. 1975, pp. 27–28.

*Primary Examiner*—Mary F. Downey
*Attorney, Agent, or Firm*—Joseph G. Kolodny

[57] ABSTRACT

Process for the production of a photographic black dye image which comprises
(a) imagewise exposing photographic silver halide material comprising at least one silver halide emulsion layer coated on a support, there being present in the silver halide emulsion layer(s) or in a layer in operative contact with at least one silver halide emulsion layer a resorcinol compound of the formula

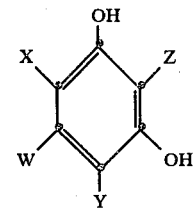

where each of W, Y and Z is hydrogen, chlorine or bromine, a nitrogen-linked heterocycle, —$SR_1$ where $R_1$ is alkyl, aryl or a heterocycle or W, Y or Z is acylamino or —$R_3$ where —$R_3$ is alkyl, cycloalkyl or aralkyl or Z alone is —CO—$R_1$ where $R_1$ is as just defined but at least one of W, Y and Z must be —$R_3$, and X which is the coupling position is hydrogen, chlorine or bromine, a nitrogen-linked heterocycle or —$SR_1$,
(b) color developing the exposed material using a color developing solution which comprises an aqueous alkaline solution of a primary aromatic amine color developing agent to form simultaneously a silver image and a black dye image,
(c) optionally bleaching the silver image, and then
(d) fixing out all the silver halide in the material using an aqueous solution of a silver halide solvent.

10 Claims, 6 Drawing Figures

PROCESS FOR THE PRODUCTION OF A PHOTOGRAPHIC IMAGE

PROCESS FOR THE PRODUCTION OF A PHOTOGRAPHIC IMAGE

This invention relates to the use of resorcinol compounds as colour couplers in photographic silver halide materials.

It has long been known that some phenolic compounds, in particular resorcinols, can be used as photographic colour couplers to yield neutral density or blackish images. However in the past the need to produce black images was not very great and little if any use was made of such phenolic colour couplers. Now, however, because of the very high cost of silver a great need has arisen to either replace silver as the image in silver halide sensitised photographic materials or to reinforce silver images by use of black dyes. Thus the prior art phenolic compounds have been re-examined but none of them have been found to yield black images of sufficiently good colour or density.

These prior art phenolic compounds and their deficiencies are described in U.S. Pat. No. 4,126,461. The subject matter of U.S. Pat. No. 4,126,461 relates to the use of certain resorcinol compounds as black colour couplers. However, whilst the resorcinol compounds described in U.S. Pat. No. 4,126,461 do yield barely acceptable black images when subjected to colour development they have been found very difficult to prepare and the separation of non-coupling or cyan-coupling by-products therefrom has been found to be very difficult.

Further, G.B. Pat. No. 1,564,349 describes m-aminophenol compounds which when colour coupled in a colour development process yield dark blue dyes having little density below 500 n.m. This renders them virtually useless either as a final image dye or as a negative image dye used in the production of positive prints. Further phenolic compounds are known from G.B. Pat. No. 2,044,474. These compounds consist of two pyrazolone nuclei linked by a 4-substituted phenol. These compounds yield a visually neutral black image when colour coupled in a colour development process but the spectrum of their colour absorption is very uneven and exhibits several peaks which renders them useless as negative images from which positive prints are printed. By black dye image is meant a dye image which absorbs light over all the visible spectrum to a substantial amount.

We have discovered that a known class of resorcinols certain members of which have been described as of use in the pharmaceutical field are of use of photographic colour couplers. These compounds when coupled in a photographic colour development process yield good dark black image dyes which can be used as the final dye image either alone or with a silver image in a positive print or which can be used to form a negative from which a positive print may be obtained.

According to the present invention there is provided a process for the production of a photographic black dye image which comprises (a) imagewise exposing photographic silver halide material comprising at least one silver halide emulsion layer coated on a support, there being present in the silver halide emulsion layer(s) or in a layer in operative contact with at least one silver halide emulsion layer a resorcinol compound of the formula

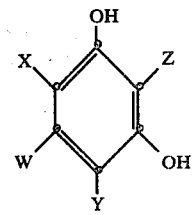

where each of W, Y and Z is hydrogen, chlorine or bromine, a nitrogen-linked heterocycle, —$SR_1$, where $R_1$ is optionally substituted alkyl having from 1 to 20 carbon atoms, optionally substituted aryl or an optionally substituted heterocycle, or W, Y or Z is a group —$NHCOR_2$ where $R_2$ is alkyl or phenyl or W, Y or Z is a group —$R_3$ where —$R_3$ is optionally substituted primary or secondary alkyl having from 1 to 20 carbon atoms of the formula

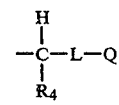

where L is an alkylene linking group —($C_mH_{2m}$)— where m is 0 to 20, $R_4$ is hydrogen or alkyl having from 1 to 20 carbon atoms, or $R_4$ together with L form a saturated 5- or 6-membered carbocyclic ring linking group, and Q is hydrogen or a group selected from —$CO_2R_5$ or —$OCOR_5$ where $R_5$ is alkyl having 1 to 20 carbon atoms, —$OR_6$ or —$CONHR_6$ or —$NHCOR_6$ where $R_6$ is alkyl having from 1 to 20 carbon atoms or is optionally substituted aryl, —$SO_3M$ where M is hydrogen or a cation, —$P(O)(OR_6)_2$ where $R_6$ is as defined above and —$NR_7R_8$ where each of $R_7$ and $R_8$ are hydrogen or optionally substituted alkyl or aryl, or $R_3$ is unsubstituted tertiary alkyl wherein the tertiary atom of the alkyl group is adjacent to the benzene ring or secondary or tertiary cycloalkyl having from 3 to 20 carbon atoms or $R_3$ is primary, secondary, or tertiary aralkyl, having from 7 to 20 carbon atoms or Z alone is —CO—$R_1$ where $R_1$ is as defined above but at least one of W, Y and Z must be —$R_3$ and X is hydrogen, chlorine or bromine, a nitrogen-linked heterocycle or —$SR_1$, where $R_1$ is as defined above, (b) colour developing the exposed material using a colour developing solution which comprises an aqueous alkaline solution of a primary aromatic amine colour developing agent to form simultaneously a silver image and a black dye image, (c) optionally bleaching the silver image, and then (d) fixing out all the silver halide in the material using an aqueous solution of a silver halide solvent.

Another object of the invention is the processed silver halide photographic material which comprises a black dye image produced by said process.

By layer in operative contact with a layer which contains silver halide is meant a layer which is close enough to the layer which contains the silver halide for oxidised colour developer to diffuse imagewise to this layer to couple with the compound of formula (1) to form a black dye image in conformity with the silver image in the silver halide layer.

The substituents W, Y and Z in the compounds of formula (1) are hydrogen or halogen such as fluorine, chlorine or bromine, preferably chlorine or bromine.

Further, W, Y and Z denote a heterocyclic ring. Preferably, this heterocyclic ring contains 5 or 6 ring atoms, at least one of which is a nitrogen atom which provides the linkage of the heterocycle to the resorcinol nucleus. Most preferably, the heterocycle has the formula

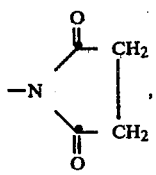

wherein the hydrogen atoms are optionally replaced by substituents such as alkyl, preferably having 1 to 4 carbon atoms, or aryl, preferably phenyl, which substituents are optionally further substituted.

W, Y and Z denote further a mercapto group of the formula —$SR_1$. $R_1$ in this formula is alkyl having preferably 1 to 20 carbon atoms such as methyl, ethyl, propyl, i-propyl, n-pentyl, 1,1-dimethylpropyl, 1,1,3,3-tetramethylbutyl, hexyl, 1-methylpentyl, neopentyl, 1-, 2- or 3-methylhexyl, heptyl, n-octyl, t-octyl, 2-ethylhexyl, n-nonyl, i-nonyl and decyl. Further, undecyl, dodecyl, tetradecyl, octadecyl and eicosyl as well as isomers thereof. These alkyl groups are optionally further substituted by, e.g., alkoxy having 1 to 10, preferably 1 to 4 carbon atoms, carbalkoxy having preferably 2 to 5 carbon atoms, phenyl or halogen. Preferred substituents for the alkyl groups are methoxy, ethoxy, propoxy, butoxy, groups of the formulae —$COOCH_3$, —$COOC_2H_5$, —$COOC_4H_9$, —$COOC_8H_{17}$, —$COOC_{12}H_{25}$, phenyl and chlorine or bromine. Preferably the alkyl groups $R_1$ contain 1 to 10, especially 5 to 10 carbon atoms. Further, $R_1$ denotes aryl which is optionally substituted. Preferred aryl groups are e.g. phenyl and naphthyl and suitable substituents for these aryl rings are e.g. the above mentioned alkoxy, carbalkoxy and halogen radicals. $R_1$ has further the meaning of a heterocyclic ring which is optionally substituted. This heterocycle preferably represents a nitrogen containing ring having 6, or preferably 5 ring atoms such as radicals of the formula

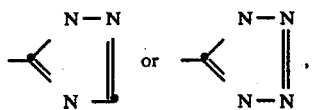

wherein the nitrogen atom adjacent to the carbon atom which provides the linkage to the resorcinol nucleus is optionally further substituted. Preferred substituents are e.g. alkyl having 1 to 4 carbon atoms, preferably methyl, or especially phenyl.

W, Y and Z are further acylamino, preferably of the formula —$NHCOR_2$, wherein $R_2$ is alkyl or aryl. Suitable alkyl groups and the substituents for these groups are listed above in the definitions of $R_1$. Alkyl radicals $R_2$ containing 1 to 10 carbon atoms, and especially methyl are mostly preferred. A suitable aryl group is phenyl. W, Y or Z further denotes a radical $R_3$ where $R_3$ is an optionally substituted primary or secondary alkyl group having 1 to 20, preferably 1 to 15 carbon atoms, which groups preferably are derivable from the formula

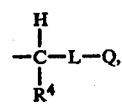

where L is an alkylene linking group of the formula —$(C_mH_{2m})$—, m being an integer of from 0 to 20, preferably from 0 to 15. The alkylene chain may be straight or branched.

$R_4$ in the above formula denotes hydrogen or alkyl, preferably containing 1 to 20 carbon atoms, more preferably 1 to 10, especially 1 to 5 carbon atoms. Suitable alkyl radicals are listed above in the definitions of $R_1$. Further, $R_4$ together with L form a carbocyclic ring, preferably 5- or 6-membered and saturated, such as cyclopentyl or cyclohexyl, which rings are optionally further substituted by phenyl or methyl, ethyl, n-propyl, i-propyl, n-butyl or t-butyl groups. Q in the above formula denotes hydrogen or one of the following substituents: acyloxy or carbalkoxy of the formulae —$CO_2R_5$ and —$OCOR_5$, wherein $R_5$ is alkyl, preferably containing 1 to 20, especially 1 to 15 and most preferably 6 to 12 carbon atoms—for suitable radicals cf. above the definitions of $R_1$—; alkoxy or carbonamido or acylamino of the formulae —$OR_6$, —$CONHR_6$ and —$NHCOR_6$, wherein $R_6$ is alkyl preferably having 1 to 20, or 1 to 10 or most preferably 1 to 5 carbon atoms or aryl such as phenyl—for suitable alkyl and aryl radicals cf. above the definitions of $R_1$—; a sulpho group of the formula —$SO_3M$, wherein M is hydrogen or a cation such as ammonium or preferably an alkali metal; a phosphoric acid ester group of the formula —$P(O)(OR_5)_2$, where $R_5$ is as defined above; and an amino group of the formula —$NR_7R_8$, where $R_7$ and $R_8$ are hydrogen or optionally substituted alkyl preferably having 1 to 5 carbon atoms or aryl groups—for suitable alkyl and aryl groups cf. above the definitions of $R_1$—. Preferably, $R_7$ and $R_8$ are each hydrogen $R_3$ is further alkyl which is preferably an unsubstituted and tertiary alkyl group. The tertiary carbon atom of the alkyl group is adjacent to the benzene ring. The alkyl groups contain preferably 3 to 20 or, more preferably, 3 to 10 or 5 to 10 carbon atoms. Such radicals are listed above in the definitions of $R_1$. Further, $R_3$ is a secondary or tertiary cycloalkyl group, preferably containing 3 to 20, especially 3 to 10 or, most preferably, 5 to 10 carbon atoms such as cyclopentyl, cyclohexyl or cyclooctyl having as a substituent an alkyl group, preferably with 1 to 4 carbon atoms. $R_3$ is further aralkyl having from 7 to 20, preferably 7 to 15 carbon atoms. The aryl moieties, preferably phenyl radicals, may be further substituted by one or more alkyl radicals, each preferably having 1 to 4 carbon atoms.

Z alone may denote a group of the formula —$COR_1$, where $R_1$ is as defined above. At least one of W, Y and Z must be —$R_3$ which is as defined above.

X denotes the coupling position and is hydrogen or halogen such as chlorine, bromine or iodine, preferably chlorine or bromine, further a nitrogen-linked heterocycle or the mercapto group —$SR_1$. Such radicals are defined above in the definitions of W, Y and Z.

Suitable compounds of the formula (1) for use in the inventive process are those wherein W, Y and Z are hydrogen, chlorine, bromine, a radical of the formula

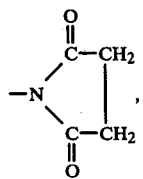

wherein the hydrogen atoms are optionally replaced by alkyl having 1 to 4 carbon atoms or phenyl, or W, Y and Z are —SR$_1$, wherein R$_1$ is alkyl having 1 to 20 carbon atoms, optionally substituted by alkoxy having 1 to 10 carbon atoms, carbalkoxy having 2 to 5 carbon atoms, phenyl or halogen, or R$_1$ is phenyl optionally substituted by alkoxy having 1 to 10 carbon atoms, carbalkoxy having 2 to 5 carbon atoms, phenyl or halogen, or R$_1$ is a radical of the formula

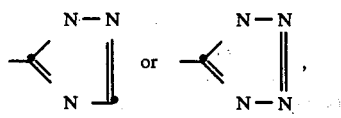

wherein the nitrogen atom adjacent to the carbon atom which provides the linkage to the resorcinol nucleus is optionally substituted by alkyl having 1 to 4 carbon atoms or phenyl, or W, Y or Z is a group —NHCOR$_2$, where R$_2$ is alkyl having 1 to 20 carbon atoms or phenyl, optionally substituted by alkoxy having 1 to 10 carbon atoms, carbalkoxy having 2 to 5 carbon atoms, phenyl or halogen or W, Y or Z is a group —R$_3$ where —R$_3$ is primary or secondary alkyl having from 1 to 15 carbon atoms of the formula

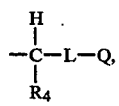

where L is an alkylene linking group of the formula —(C$_m$H$_{2m}$)—, m being an integer of from 0 to 15, R$_4$ is hydrogen, alkyl having 1 to 10 carbon atoms or forms together with L a cyclopentyl or cyclohexyl ring which is optionally substituted or phenyl, methyl, ethyl, n-propyl, i-propyl, n-butyl or t-butyl, Q is hydrogen or —CO$_2$R$_5$ or —OCOR$_5$ where R$_5$ is alkyl having 1 to 20 carbon atoms; —OR$_6$, —CONHR$_6$ or —NHCOR$_6$ where R$_6$ is alkyl having 1 to 10 carbon atoms or phenyl optionally substituted by alkyl groups each having 1 to 10 carbon atoms, —SO$_3$M where M is hydrogen, ammonium or an alkali metal; —P(O)(OR$_6$)$_2$, where R$_6$ is as defined above; or —NR$_7$R$_8$ where R$_7$ and R$_8$ are hydrogen, alkyl having 1 to 5 carbon atoms or phenyl; or R$_3$ is unsubstituted tertiary alkyl having 3 to 10 carbon atoms or R$_3$ is secondary or tertiary cycloalkyl having 3 to 10 carbon atoms, or R$_3$ is aralkyl having 7 to 20 carbon atoms, or Z alone is —COR$_1$ where R$_1$ is as defined above but at least one of W, Y and Z must be —R$_3$, X is hydrogen, chlorine, a radical of the formula

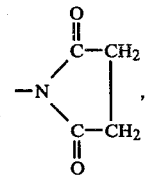

wherein the hydrogen atoms are optionally replaced by alkyl having 1 to 4 carbon atoms or phenyl, or X is —SR$_1$ where R$_1$ is as defined above.

More suitable compounds of the formula (1) for use in the inventive process are those wherein W, Y and Z are hydrogen, chlorine, bromine, a radical of the formula

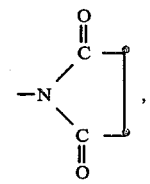

—SR$_1$ wherein R$_1$ is alkyl having 1 to 10 carbon atoms or phenyl or a radical of the formula

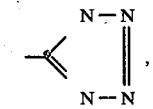

wherein the nitrogen atom adjacent to the carbon atom which provides the linkage to the resorcinol nucleus is optionally substituted by phenyl or methyl, or W, Y or Z is —NHCOR$_2$ where R$_2$ is alkyl having 1 to 10 carbon atoms or phenyl or W, Y or Z is a group —R$_3$ where —R$_3$ is primary or secondary alkyl having 1 to 15 carbon atoms of the formula

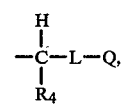

where L is —(C$_m$H$_{2m}$)—, m is as defined in claim 2, R$_4$ is hydrogen, alkyl having 1 to 5 carbon atoms or forms together with L is a cyclopentyl or cyclohexyl ring optionally substituted by phenyl, methyl or t-butyl, Q is hydrogen, —CO$_2$R$_5$ or —OCOR$_5$ where R$_5$ is alkyl having 6 to 12 carbon atoms; —OR$_6$, —CONHR$_6$ or —NHCOR$_6$ where R$_6$ is alkyl having 1 to 5 carbon atoms or phenyl; —SO$_3$M where M is hydrogen or an alkali metal; —P(O)(OR$_6$)$_2$, where R$_6$ is as defined above; and —NR$_7$R$_8$ where R$_7$ and R$_8$ are hydrogen, alkyl having 1 to 5 carbon atoms or phenyl; or R$_3$ is unsubstituted tertiary alkyl having 5 to 10 carbon atoms or secondary or tertiary cycloalkyl having 5 to 10 carbon atoms, or R$_3$ is aralkyl having 7 to 15 carbon atoms, or Z alone is —COR$_1$ where R$_1$ is as defined above but at least one of W, Y and Z must be —R$_3$, X is hydrogen, chlorine, bromine or —SR$_1$ where R$_1$ is as defined above.

Most preferably the compounds of the formula (1) for use in the inventive process are those wherein W, Y and Z are hydrogen, chlorine, bromine, or W, Y or Z is —NHCOR$_2$ where R$_2$ is methyl, phenyl, or a group —R$_3$ where —R$_3$ is primary or secondary alkyl having 1 to 15 carbon atoms of the formula

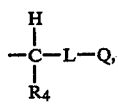

where L is —(C$_m$H$_{2m}$)—, m is as defined in claims 3, R$_4$ is hydrogen, methyl or forms together with L a cycloalkyl ring optionally substituted by t-butyl, Q is hydrogen, —CO$_2$R$_5$ where R$_5$ is alkyl having 5 to 15 carbon atoms, —OR$_6$ where R$_6$ is phenyl optionally substituted by alkyl groups each having 4 to 8 carbon atoms, or amino or —NHCOCH$_3$ or —NHCOC$_6$H$_5$; or R$_3$ is unsubstituted tertiary alkyl having 5 to 8 carbon atoms or R$_3$ is secondary or tertiary cycloalkyl having 5 to 10 carbon atoms or aralkyl having 7 to 15 carbon atoms, at least one of W, Y and Z must be —R$_3$, and Y is hydrogen, chlorine bromine or a radical of the formula

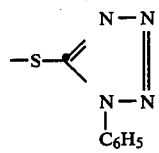

Preferably in the compounds of formula (1), X and Z are hydrogen.

In another preferred group of the compounds of formula (1), X, W and Z are all hydrogen and Y is the primary or secondary alkyl group R$_3$ defined above or the unsubstituted tertiary alkyl group R$_3$ defined above.

Suitable primary aromatic amine colour developing agents for use in the inventive process are p-phenylenediamine compounds, for example 4-amino-N,N-dimethylaniline hydrochloride, 4-amino-N,N-diethylaniline hydrochloride, 4-amino-3-methyl-N,N-diethylaniline hydrochloride and p-aminophenol compounds for example a p-aminophenol itself and 2,6-dichloro-4-aminophenol.

Where a silver bleach step is employed this may be combined with the fixing step by employing a bleach-fix or blix bath.

Especially useful compounds are those where X, W and Z are hydrogen atoms and Y is primary or secondary alkyl having 1 to 15 carbon atoms of the formula

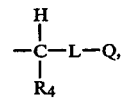

where L is —(C$_m$H$_{2m}$)—, m is as defined above, R$_4$ is hydrogen, methyl or forms together with L a cyclohexyl ring optionally substituted by t-butyl, Q is hydrogen, —CO$_2$R$_5$ where R$_5$ is alkyl having 5 to 15 carbon atoms, —OR$_6$ where R$_6$ is phenyl optionally substituted by alkyl groups each having 4 to 8 carbon atoms, or amino or —NHCOCH$_3$ or —NHCOC$_6$H$_5$ or unsubstituted tertiary alkyl having 5 to 8 carbon atoms. Most preferably Y is an alkyl group having at least 12 carbon atoms.

It is to be understood that all the substituents W, Y and Z can influence the spectral absorption of the black dye of the coupled resorcinol compounds of formula (1). However, the substituent X cannot influence the spectral absorption of the dye as this substituent leaves during the coupling reaction. However, the substituent can affect the coupling rate and sometimes increased coupling activity is obtained when X is either a chlorine or bromine rather than a hydrogen atom. The group —SR$_1$ may be a so-called development inhibiting group and sometimes it is preferred to include a D.I.R. resorcinol coupler of this type in the photographic material to cause inter- and intra-image effects such as image edge-enhancement. The use of D.I.R. couplers is extremely well known in the art as described for example in U.S. Pat. No. 3,418,062, U.S. Pat. No. 3,227,554 and G.B. Pat. No. 1,293,640.

In the process of the present invention the photographic material which comprises in a layer thereof a compound of formula (1) is processed after exposure by a colour development process using a primary aromatic amine colour developing agent of known type. As usual in colour development processes the primary aromatic amine developing agent reduces the latent silver image to form a silver image and becomes oxidised, and the oxidised colour developers couples with the resorcinol colour coupler of formula (1) to form a black dye image in conformity with the black silver image. In some instances the density of the black dye is sufficient to form the final image in the material and in such a case the developed silver is bleached and the silver halide is fixed out to recover all the silver.

In other cases it is preferred to use the black dye image to reinforce the silver image and so reduce the silver content in the original material.

This resorcinol compound is preferably incorporated into the silver halide emulsion as an oil dispersion.

Examples of particularly useful compounds of formula (1) are the following compounds:

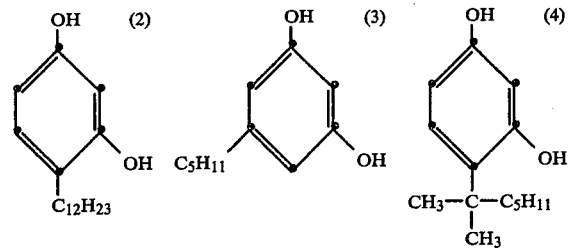

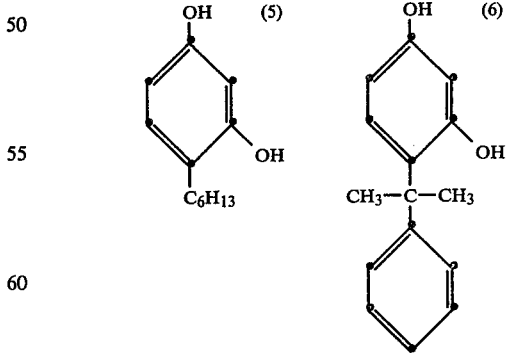

Other useful compounds are those of the following formulae:

(7)  (8)

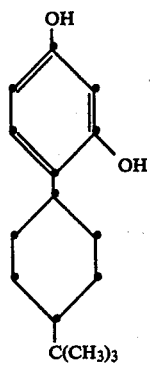
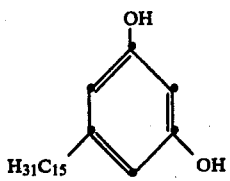
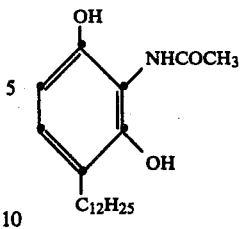
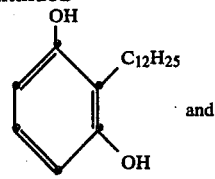
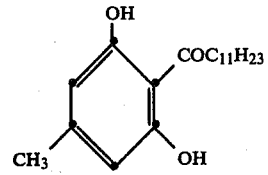
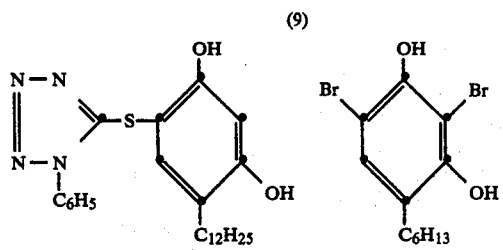
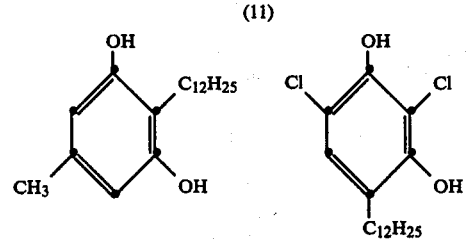
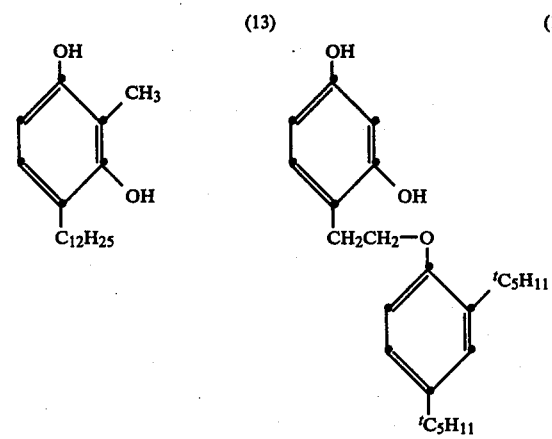
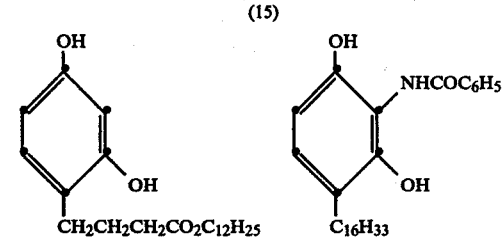
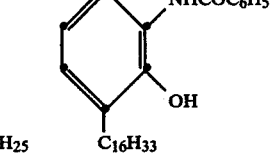

The method of synthesis of the resorcinols of formula (1) are well documented for example in C. J. Baylis, S. W. Odle and J. H. P. Tyman, J. C. S. Perkin 1, 1981, 132; R. S. Marmor J. Org. Chem., 1972, 37, 2901; Houben-Weyl, "Methoden der Organischen Chemie", Vol. 6, Part 1c (Georg Thieme. Stuttgart, 1976); S. Coffey, Rodd's "Chemistry of Carbon Compounds", 2nd Edn., Vol. 3, Part A (Elsevier, Amsterdam, 1971); E. Biller, W. R. Carmichael and C. Richter, CHEM. and Ind. Synthesis, 1973, 685; N. Schamp, R. Verke and L. De Buyck, Tetrahedron, 1973, 29, 3857; and B.P. 1,579,557. Any novel compounds covered by formula (1) may be produced by analogous methods.

Synthesis of nuclear-substituted resorcinols (e.g. by halogen, mercaptan) can also be achieved by well-known routes in, for example, Rodd (see above).

PREPARATIONS

Preparation 1.

Compound of the formula (2) was prepared as follows:

(i) 4-Dodecanoyl resorcinol 68 g of granular zinc chloride and 250 g of lauric acid were melted togerther at 125° C., under nitrogen and with protection from moisture by calcium chloride. The mass was stirred and 55 g of resorcinol were added portionwise over 15 minutes. The mixture was stirred a further 2 hours, cooled and drowned in 500 ml of water. 100 ml of chloroform was added to break up the solid mass, and the crystalline solid remaining was filtered, washed with chloroform, then water, to give 60.4 g of a solid with a melting point of from 79°-83° C. This was used without further purification. The analytical sample was recrystallised from light petroleum (b.p. 60°-80° C.). The pure product had a melting point of from 83.5°-85° C.

(ii) 4-Dodecyl resorcinol 29.2 g of the product from (i) in 200 ml of acetic acid was added to 300 ml of 6 M hydrochloric acid to give a fine precipitate. To this was assed a zinc amalgam (made by intimately mixing 60 g of zinc, 6 g of mercury (II) chloride, 5 ml of conc. hydrochloric acid and 90 ml of water over 20 minutes. The mixture was heated at reflux for 5 hours; three further portions of 60 ml of conc. hydrochloric acid being added. After cooling, the filtered solids were taken up in chloroform, refiltered, and washed with 6 M hydrochloric acid, then water, dried and evaporated to give 26 g of the crude product. This was recrystallised from light petroleum (b.p. 60°–80° C.) to give 22.9 g of the product with a melting point of from 81°–82.5° C.

Preparation 2

Compound of the formula (4) was prepared as follows:

To 100 parts of glacial acetic acid containing 9.8 parts of 98% sulphuric acid was added 22 parts of resorcinol followed by 13 parts of 2-hydroxy-2-methyl-heptane at room temperature. After storing overnight at the same temperature the reaction mixture was poured into 1000 parts of water. The organic phase which separated out, was after decanting off the water, taken up in ether, washed with sodium bicarbonate solution, and finally with water. The ether solution was then evaporated and the residue distilled to give 2-(2,4-dihydroxyphenyl)-2-methyl-heptane (compound of the formula (4)) with a boiling point (b.p.$_{12}$) of from 202°–204° C. and with the following percentage composition by weight:

|  | Carbon | Hydrogen |
| --- | --- | --- |
| Found | 75.59 | 10.24 |
| Calculated for $C_{14}H_{22}O_2$ | 75.63 | 9.97 |

In a similar manner but starting from α-methylstyrene instead of 2-hydroxy-2-methyl hexane there was prepared 4-(1,1-dimethylbenzyl)-resorcinol (m.p. 128°–130° C.). This is the compound of the formula (6). The compounds of the formulae (3) and (5) were purchased from the Aldrich Chemical Co. Ltd. of the U.S.A.

The amounts of the compound of formula (1) present in the photographic material depend on wether the photographic material which incorporates the compound is designed to be processed so that the silver image remains or is removed to leave only the black image. A suitable amount of compound (1) to be present in a negative film material in which no silver image is left is 50 to 100 mg/dm$^2$ and in which the silver image is retained is 25 to 50 mg/dm$^2$.

Suitable amounts of the compound of formula (1) to be present in positive print material in which no silver is left are 20 to 40 mg/dm$^2$ and in which the silver image is retained are 10 to 20 mg/dm$^2$.

When the photographic material is to be used as a positive print material most preferably the silver image is left so that the black dye enhances the silver image but does not wholly replace it. Preferably such material comprises one silver halide emulsion layer which contains a compound of formula (1). This resorcinol compound is preferably incorporated into the silver halide emulsion as an oil dispersion. Suitable silver coating weights for such silver halide emulsion layers are 2 to 15 mg/dm$^2$.

When photographic material is to be used as an X-ray film there is usually one silver halide emulsion layer coated on each side of the transparent film base and present in each silver halide emulsion layer is a compound of formula (1). Usually such X-ray film material is processed to leave the silver image so that the black dye image reinforces the silver image. Suitable silver halide coating weights of such silver halide emulsion layers are 50 to 100 mg/dm$^2$.

Any of the silver halides used in photographic materials can be used in the photographic material used in the present invention, for example silver chlorobromide, silver chloride, silver iodobromide, silver bromide and silver iodobromochloride.

The silver halide crystals may be chemically sensitised by any of the well-known means, for example by use of sulphur, selenium and noble metals. Examples of suitable sensitising compounds are sodium thiosulphate and mercury, gold, palladium and platinum salts.

The emulsions used in the photographic material used in the present invention may be optically sensitised by the addition of optical sensitisers, for example carbocyanine and merocyanine dyes, to the emulsions.

These emulsions may contain any of the additives commonly used in photographic emulsion, for example wetting agents, stabilising agents, polyethylene oxides, metal sequestering agents and growth or crystal habit modifying agents commonly used for silver halide such as adenine.

Preferably the dispersing medium is gelatin or a mixture of gelatin and a water-soluble polymer, for example a latex vinyl acrylate-containing polymer. Most preferably if such a latex is present in the final emulsion it is added after all the crystal growth has occurred. However other water-soluble colloids, for example casein, polyvinylpyrrolidine or polyvinyl alcohol, may be used alone or together with gelatin.

The support used in the photographic material according to the present invention may be any one of the bases commonly used for photographic materials, for example baryta coated paper base, polyethylene laminated paper base, cellulose triacetate, cellulose acetate butyrate and subbed and axially oriented polyethylene terephthalate.

EXAMPLE 1

Formulation of the compound of the formula (2) as an oil dispersion

A. 1 g of the compound of the formula (2) is dissolved in 1 g isopropylated phenyl phosphate and 1 g ethyl acetate mixture, by heating under reflux; cool to 50° C.

B. 1 ml 10% (v/v in water) sulphonated PEO wetting agent and 3 ml distilled water are added to 8 g to 10% (w/w in water, pH 6.5) deionised gelatin at about 50° C.

A and B are then mixed with hand stirring and are dispersed on an ultrasonic mixer for about 30 seconds.

Formulation for coating 0.45 g of the above coupler dispersion are added to 1.70 g 10% deionised gel solution and 0.54 g of a 9.2% iodide silver iodobromide emulsion. The emulsion contains 162 g silver and 100 g gel in 1467 g total weight. Triazine hardener is added to the formulation at 20 mole/$10^5$ g gel. After adequate mixing, the coating formulation is spread by hand on to 2.4 dm$^2$ polyester base, maintained at 40° C. during coating. Coupler and silver coating weights are approximately 25 mg/dm$^2$ with a gel coating weight of about 80 mg/dm$^2$. Coatings are dried and then incubated for about 12 hours at 45° C., 65% R.H. The coatings were overall exposed to white light for 10 seconds and processed as follows at 38° C.

Development (5 minutes)
  0.37 g $K_2CO_3$
  1.5 ml $K_2SO_3$, 65% solution
  1.05 g KBr
  6.0 ml DTPA (37% solution)
  2 g Hydroxylamine sulphate
  1 ml $H_2SO_4$ (5 N)

2.40 g CD4
1.33 g Na₂S₂O₅
0.94 ml Acetic acid (80% w/v)
H₂O to 1 liter. pH 10.20
Bleaching (6½ minutes)
  Ammonium bromide: 150 g

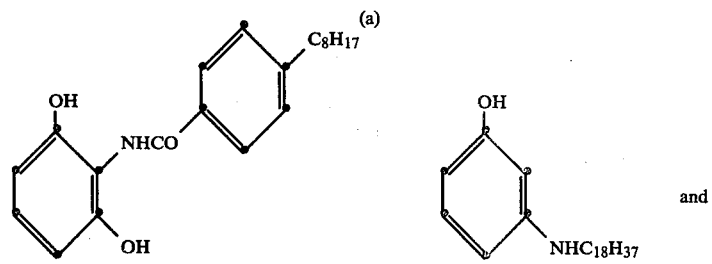

according to U.S. Pat. No. 4.126.461    according to U.S. Pat. No. 1.564.349

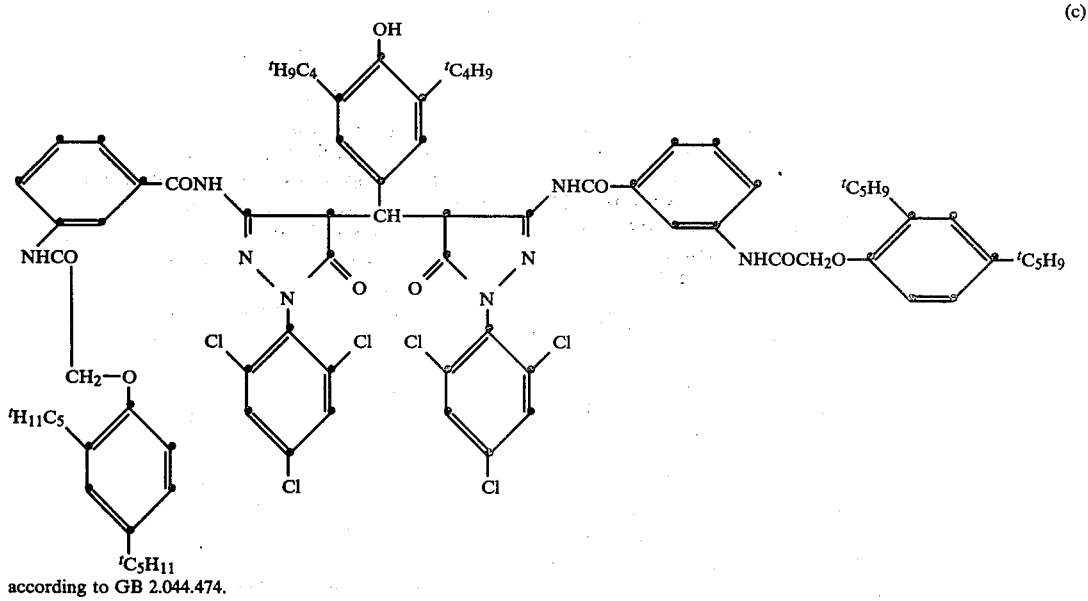

according to GB 2.044.474.

Ferric ammonium EDTA: 112 g
EDTA: 2.5 g
Sodium nitrate: 35 g
Acetic acid, glacial: 10 ml
Water to: 1 liter
pH 6.0±0.2
Fixing (6½ minutes)
  Ammonium thiosulphate: 130 g
  Disodium EDTA: 1.25 g
  Sodium metabisulphite: 12 g
  Sodium hydroxide: 2 g
  pH 6.5±0.2
Washing (3 minutes at 38° C.).
CD4 is 4 N-ethyl-N-(2'-hydroxyethyl)amino-2-methylaniline hydrosulphate
EDTA is Ethylenediamine tetra-acetic acid
DTPA is Diethylenetriamine penta-acetic acid.

It is possible, to combine the silver bleach step with the fixing step using the corresponding bleach-fix (blix) bath. The attached absorption spectrum shows that a very black dye is obtained which absorbs very well over the entire visible spectrum.

The compounds of the formulae (3) to (6) were formulated as the compound of the formula (2) and after coating, exposure and processing a black dye was obtained in each sample of photographic material which included these compounds.

The absorption spectra obtained are attached hereto.

Figure 2:
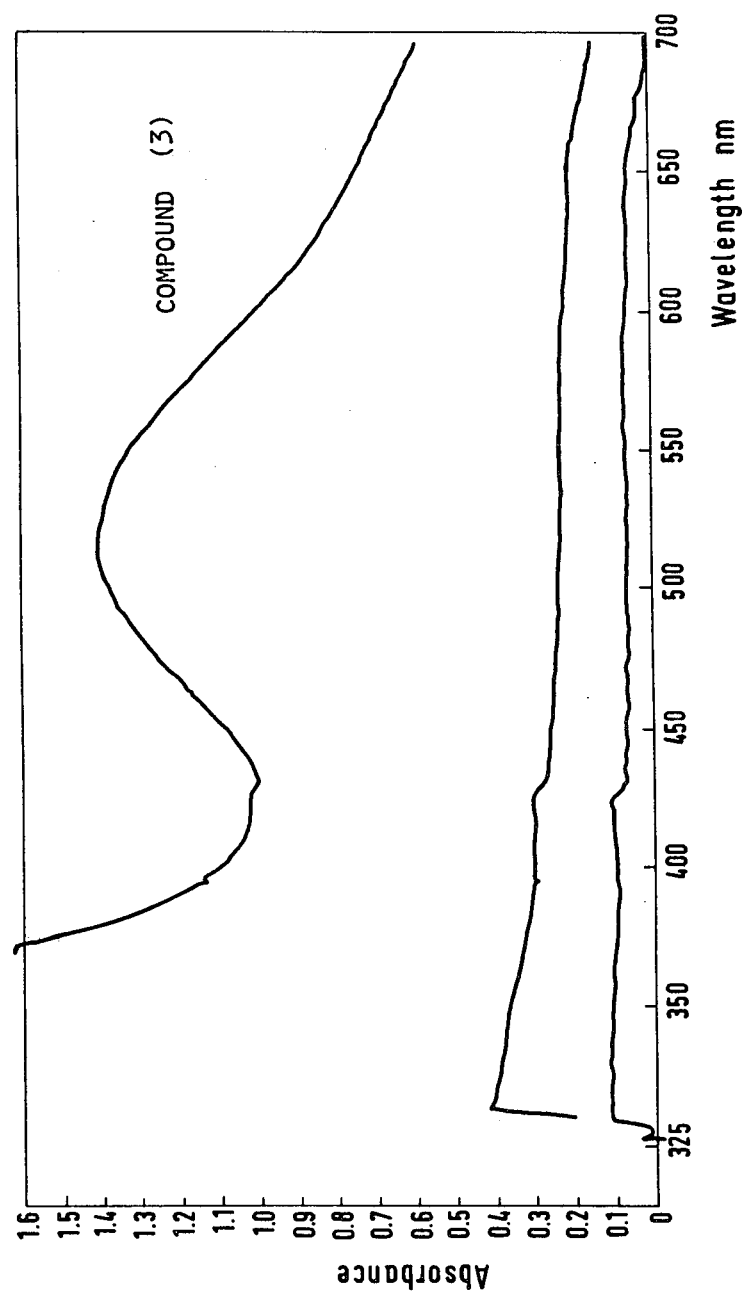
Figure 3:
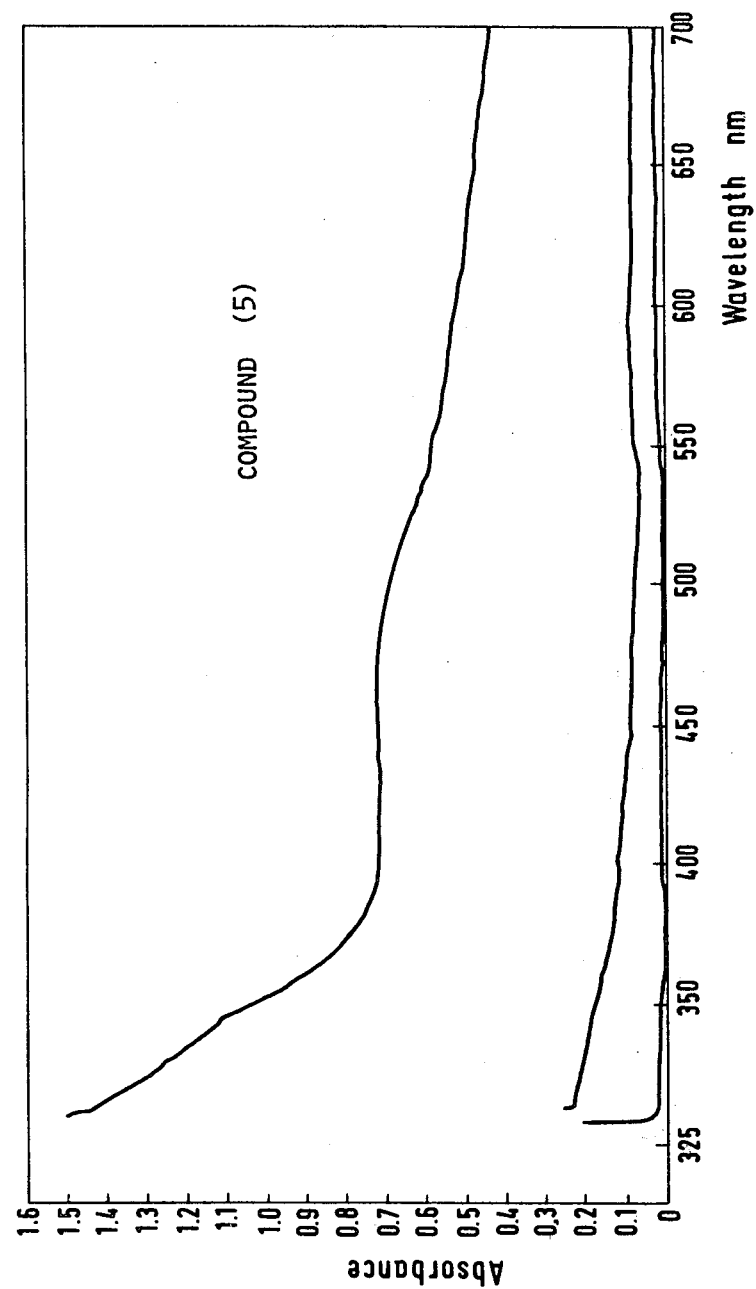
Figure 4:
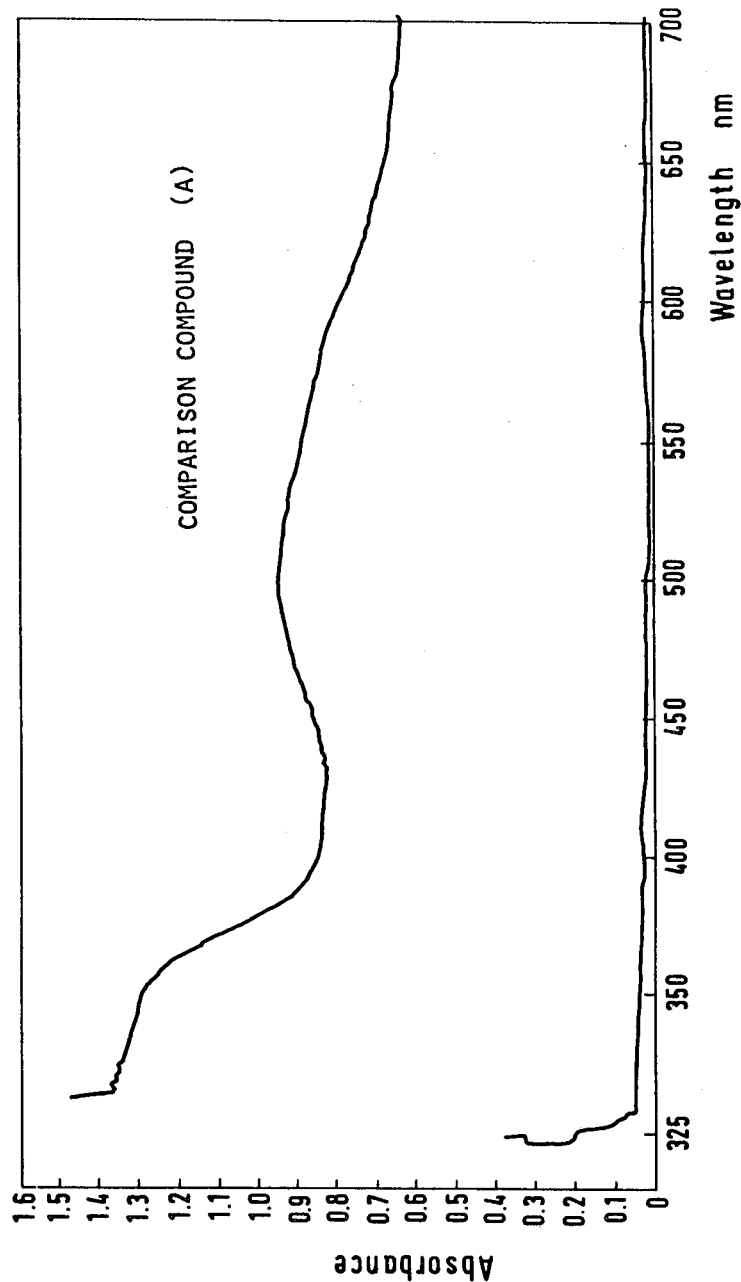
Figure 5:
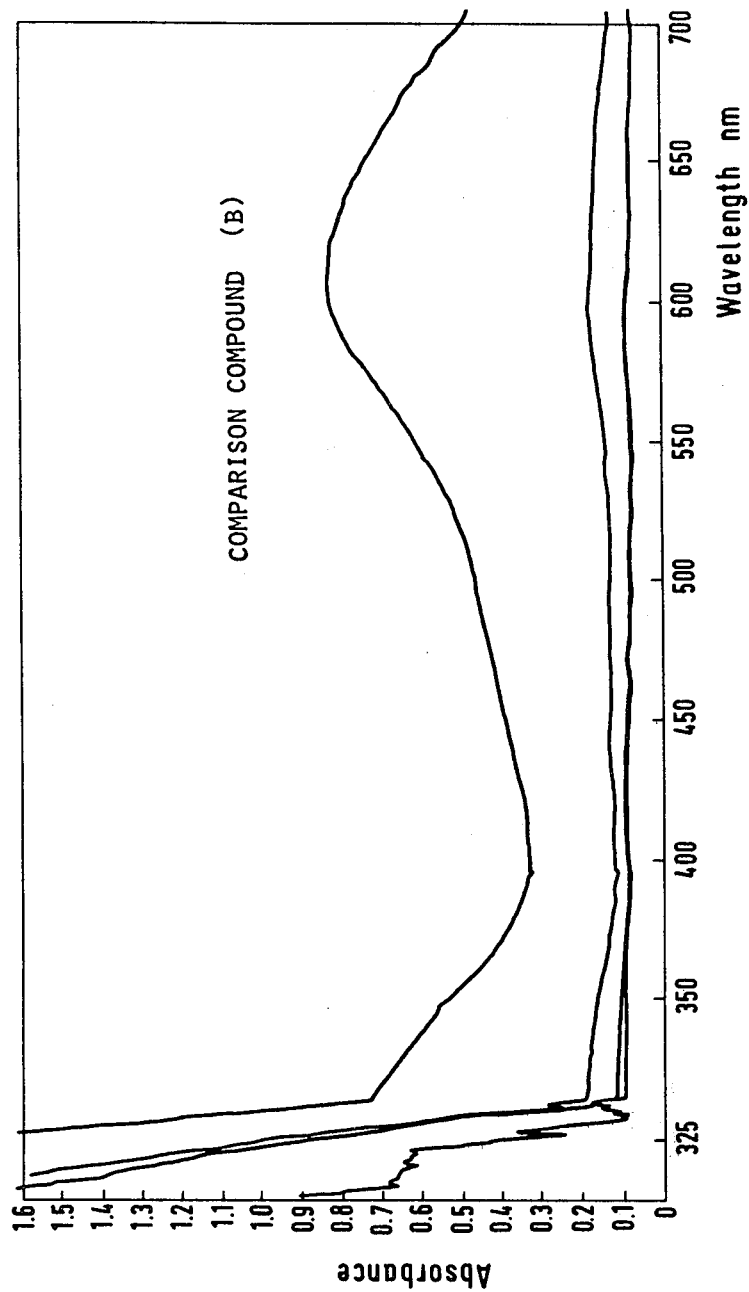
Figure 6:
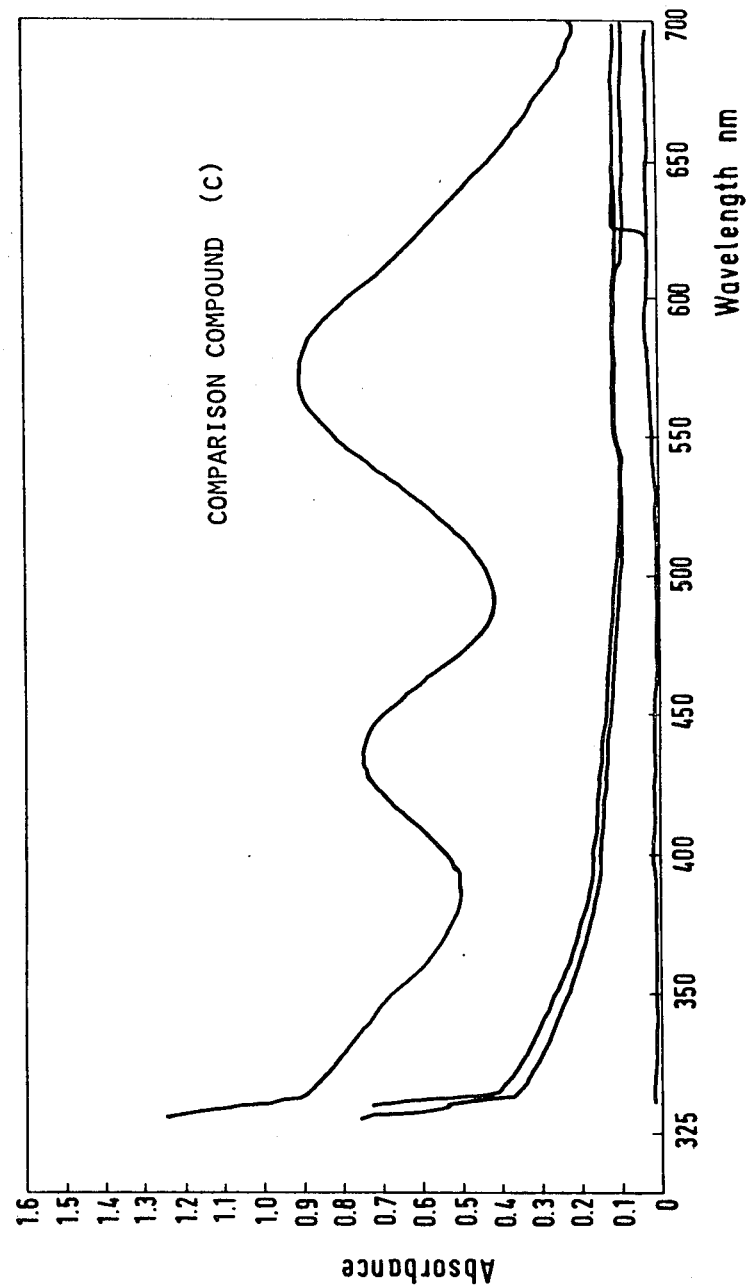

FIGS. 1 to 3 show the absorption spectra of compounds (2), (3) and (5). FIGS. 4 to 6 show the absorption spectra of the comparison compounds

I claim:

1. A process for the production of a photographic black dye image which comprises
(a) imagewise exposing photographic silver halide material comprising at least one silver halide emulsion layer coated on a support, there being present in the silver halide emulsion layer (s) or in a layer in operative contact with at least one silver halide emulsion layer, a colour coupler consisting essentially of at least one compound of the formula

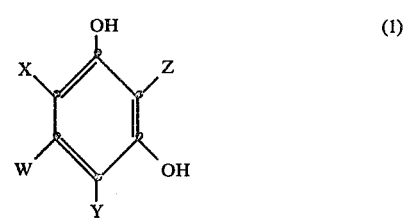

where each of W, Y and Z is hydrogen, chlorine or bromine, a nitrogen-linked heterocyclic, —SR₁, where R₁ is optionally substituted alkyl having from 1 to 20 carbon atoms, optionally substituted aryl or an optionally substituted heterocycle or W, Y or Z is a group —R₃ where —R₃ is optionally substituted primary or secondary alkyl having from 1 to 20 carbon atoms of the formula

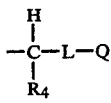

where L is an alkylene linking group —(CH₂)ₘ— where m is 0 to 20, R₄ is hydrogen, alkyl having from 1 to 20 carbon atoms, or R₄ together with L form a saturated 5- or 6-membered carbocyclic ring linking group, and Q is hydrogen or a group selected from —CO₂R₅ or —OCOR₅ where R₅ is alkyl having from 1 to 20 carbon atoms; —OR₆ or —CONHR₆ or —NHCOR₆ where R₆ is an alkyl group having from 1 to 20 carbon atoms or is an optionally substituted aryl group; —SO₃M where M is hydrogen or a cation; —P(O)(OR₅)₂ where R₅ is as defined above; or —NR₇R₈ where each of R₇ and R₈ are hydrogen or optionally substituted alkyl or aryl; or R₃ is unsubstituted tertiary alkyl, wherein the teriary atom of the alkyl group is adjacent to the benzene ring or secondary or tertiary cycloalkyl having from 3 to 20 carbon atoms or R₃ is primary, secondary or tertiary aralkyl, having from 7 to 20 carbon atoms, or Z alone is —CO—R₁ where R₁ is as defined above but at least one of W, Y and Z must be —R₃, and X is hydrogen, chlorine or bromine, a nitrogen-linked heterocycle or —SR₁ where R₁ is as defined above, (b) colour developing the exposed material using a colour developing solution which comprises an aqueous alkaline solution of a primary aromatic amine colour developing agent to form simultaneously a silver image and a black dye image, (c) optionally bleaching the silver image, and then (d) fixing out all the silver halide in the material using an aqueous solution of a silver halide solvent.

2. A process according to claim 1 where in the resorcinol compound of the formula (1) W, Y and Z are hydrogen, chlorine, bromine, a radical of the formula

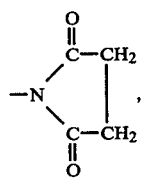

wherein the hydrogen atoms are optionally replaced by alkyl having 1 to 4 carbon atoms or phenyl, or W, Y and Z are —SR₁, wherein R₁ is alkyl having 1 to 20 carbon atoms, optionally substituted by alkoxy having 1 to 10 carbon atoms, carbalkoxy having 2 to 5 carbon atoms, phenyl or halogen, or R₁ is phenyl optionally substituted by alkoxy having 1 to 10 carbon atoms, carbalkoxy having 2 to 5 carbon atoms, phenyl or halogen, or R₁ is a radical of the formula

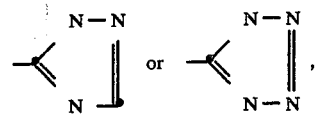

wherein the nitrogen atom adjacent to the carbon atom which provides the linkage to the resorcinol nucleus is optionally substituted by alkyl having 1 to 4 carbon atoms or phenyl, or W, Y or Z is a group —R₃ where —R₃ is primary or secondary alkyl having from 1 to 15 carbon atoms of the formula

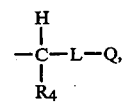

where L is an alkylene linking group of the formula —(CₘH₂ₘ)—, m being an integer of from 0 to 15, R₄ is hydrogen, alkyl having 1 to 10 carbon atoms or forms together with L a cyclopentyl or cyclohexyl ring which is optionally substituted by phenyl, methyl, ethyl, n-propyl, i-propyl, n-butyl or t-butyl, Q is hydrogen or —CO₂R₅ or —OCOR₅ where R₅ is alkyl having 1 to 20 carbon atoms; —OR₆, —CONHR₆ or —NHCOR₆ where R₆ is alkyl having 1 to 10 carbon atoms or phenyl optionally substituted by alkyl groups each having 1 to 10 carbon atoms, —SO₃M where M is hydrogen, ammonium or an alkali metal; —P(O)(OR₆)₂, where R₆ is as defined above; or —NR₇R₈ where R₇ and R₈ are hydrogen, alkyl having 1 to 5 carbon atoms or phenyl; or R₃ is unsubstituted tertiary alkyl having 3 to 10 carbon atoms or R₃ is secondary or tertiary cycloalkyl having 3 to 10 carbon atoms, or R₃ is aralkyl having 7 to 20 carbon atoms, or Z alone is —COR₁ where R₁ is as defined above but at least one of W, Y and Z must be —R₃, X is hydrogen, chlorine, a radical of the formula

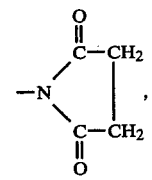

wherein the hydrogen atoms are optionally replaced by alkyl having 1 to 4 carbon atoms or phenyl, or X is —SR₁ where R₁ is as defined above.

3. A process according to claim 2 where in the resorcinol compound of the formula (1) W, Y and Z are hydrogen, chlorine, bromine, a radical of the formula

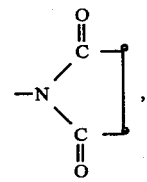

—SR₁ wherein R₁ is alkyl having 1 to 10 carbon atoms or phenyl or a radical of the formula

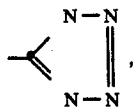, wherein the nitrogen atom adjacent to the carbon atom which provides the linkage to the resorcinol nucleus is optionally substituted by phenyl or methyl, or W, Y or Z is a group —$R_3$ where —$R_3$ is primary or secondary alkyl having 1 to 15 carbon atoms of the formula

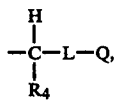

where L is —$(C_mH_{2m})$—, m is as defined in claim 2, $R_4$ is hydrogen, alkyl having 1 to 5 carbon atoms or forms together with L a cyclopentyl or cyclohexyl ring optionally substituted by phenyl, methyl or t-butyl, Q is hydrogen, —$CO_2R_5$ or —$OCOR_5$ where $R_5$ is alkyl having 6 to 12 carbon atoms; —$OR_6$, —$CONHR_6$ or —$NHCOR_6$ where $R_6$ is alkyl having 1 to 5 carbon atoms or phenyl; —$SO_3M$ where M is hydrogen or an alkali metal; —$P(O)(OR_6)_2$, where $R_6$ is as defined above; and —$NR_7R_8$ where $R_7$ and $R_8$ are hydrogen, alkyl having 1 to 5 carbon atoms or phenyl; or $R_3$ is unsubstituted tertiary alkyl having 5 to 10 carbon atoms or secondary or tertiary cycloalkyl having 5 to 10 carbon atoms, or $R_3$ is aralkyl having 7 to 15 carbon atoms, or Z alone is —$COR_1$ where $R_1$ is as defined above but at least one of W, Y and Z must be —$R_3$, X is hydrogen, chlorine, bromine or —$SR_1$ where $R_1$ is as defined above.

4. A process according to claim 3 where in the resorcinol compound of the formula (1) W, Y and Z are hydrogen, chlorine, bromine, or a group —$R_3$ where —$R_3$ is primary or secondary alkyl having 1 to 15 carbon atoms of the formula

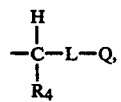

where L is —$(C_mH_{2m})$—, m is as defined in claims 3, $R_4$ is hydrogen, methyl or forms together with L a cyclohexyl ring optionally substituted by t-butyl, Q is hydrogen, —$CO_2R_5$ where $R_5$ is alkyl having 5 to 15 carbon atoms, —$OR_6$ where $R_6$ is phenyl optionally substituted by alkyl groups each having 4 to 8 carbon atoms, or amino or —$NHCOCH_3$ or —$NHCOC_6H_5$; or $R_3$ is unsubstituted tertiary alkyl having 5 to 8 carbon atoms or $R_3$ is secondary or tertiary cycloalkyl having 5 to 10 carbon atoms or aralkyl having 7 to 15 carbon atoms, at least one of W, Y and Z must be —$R_3$, and Y is hydrogen, chlorine bromine or a radical of the formula

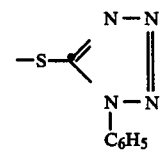

5. A process according to claim 4 where in the resorcinol compound of formula (1) both X and Z are hydrogen.

6. A process according to claim 4 where in the resorcinol compound of formula (1) X, W and Z are hydrogen and Y is primary or secondary alkyl having 1 to 15 carbon atoms of the formula $$-\underset{R_4}{\underset{|}{\overset{H}{\overset{|}{C}}}}-L-Q,$$

where L is —$(C_mH_{2m})$—, m is as defined in claim 3, $R_4$ is hydrogen, methyl or forms together with L a cyclohexyl ring optionally substituted by t-butyl, Q is hydrogen, —$CO_2R_5$ where $R_5$ is alkyl having 5 to 15 carbon atoms, —$OR_6$ where $R_6$ is phenyl optionally substituted by alkyl groups each having 4 to 8 carbon atoms, or amino or —$NHCOCH_3$ or —$NHCOC_6H_5$ or unsubstituted tertiary alkyl having 5 to 8 carbon atoms.

7. A process according to claim 1 wherein the resorcinol compound of formula (1) is present in the silver halide emulsion layer.

8. A process according to claim 1 wherein the silver bleach step is combined with the fixing step by employing a bleach-fix bath.

9. A process according to claim 1 wherein the primary aromatic amine colour developing agent is a p-phenylenediamine or a p-aminophenol compound.

10. A process according to claim 1 wherein the compound of formula (1) is incorporated into the silver halide emulsion in an oil dispersion.

* * * * *